Jan. 12, 1954
C. C. O'NEAL
ROSE PLANT
Filed Oct. 31, 1952
Plant Pat. 1,240
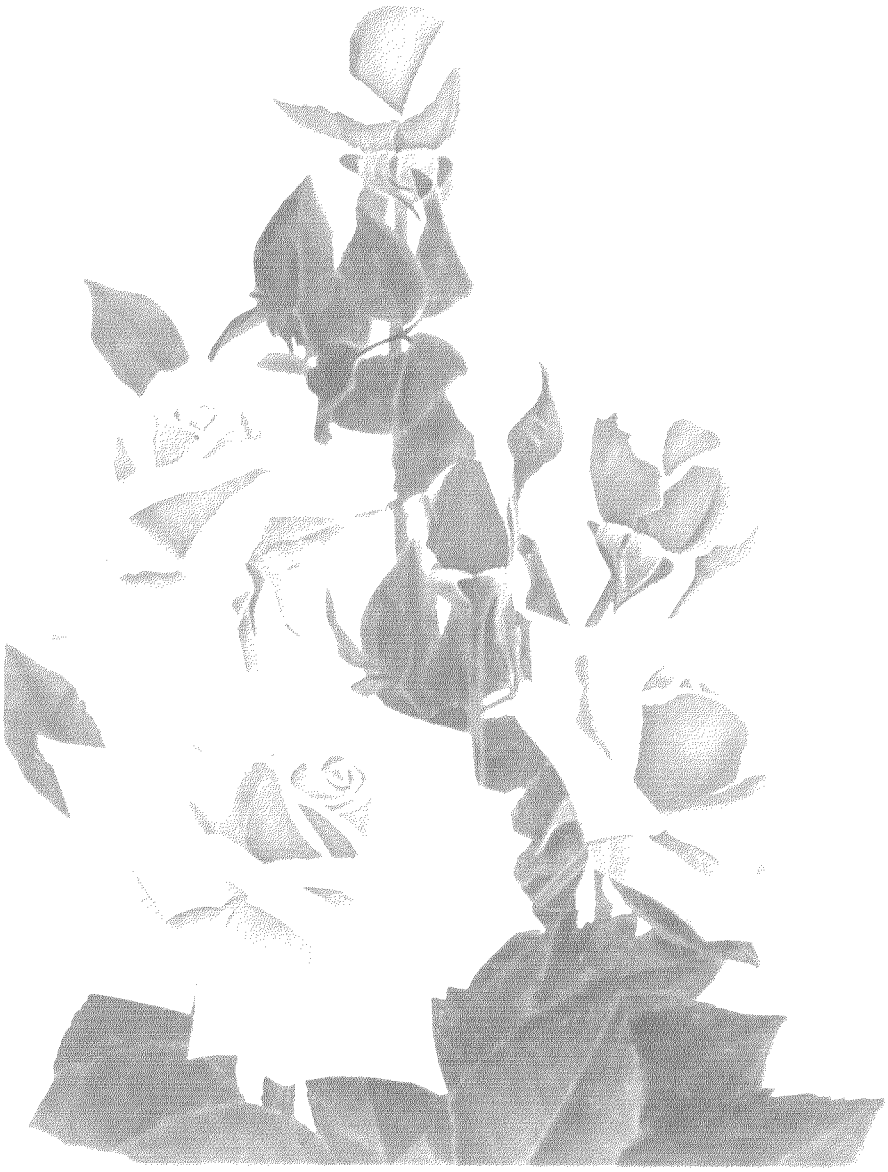
INVENTOR
Conrad C. O'Neal
by Orville M. Kelly
Plant Pat. Atty.

Patented Jan. 12, 1954 Plant Pat. 1,240

UNITED STATES PATENT OFFICE 1,240

ROSE PLANT

Conrad C. O'Neal, near North Canton, Ohio, assignor to Edith C. Bosley, Mentor, Ohio Application October 31, 1952, Serial No. 318,133

1 Claim. (Cl. 47—61)

My present invention relates to a new variety of climbing rose plant which originated from a cross made by me at my home, between the everblooming, climbing rose variety New Dawn (Plant Patent No. 1), and an unnamed hybrid tea variety. It is an entirely new type of rose plant which combines the vigor of growth of a climber, the profusion of bloom of a floribunda, and the perfection of bloom of a hybrid tea. It is an intermediate type, not previously known so far as I am aware. The bloom is very fragrant and is especially long lasting as a cut flower, both of these qualities being very unusual in a climbing rose. New foliage is predominantly red and in this respect also it differs from other climbers known to me.

This new rose variety has been asexually reproduced, by means of cuttings, by me at North Canton, Ohio, and by The Bosley Nursery in Mentor, Ohio, and its distinguishing features appear to be firmly fixed.

Accompanying illustrations show, in approximately true colors, seven buds and flowers of my new variety in different stages of opening, together with portions of the stems and foliage.

Following is a more complete description of the plant and flower of my new variety, in which color plate references indicate Ridgway's Color Standards and Nomenclature. Where plate numbers are not given, the ordinary dictionary meaning of the term is intended.

*The plant*

Growth: Very vigorous, producing large canes. Can be pruned and grown as a tall shrub rose or allowed to become a medium-growing climber. Pruning tends to make it thick and heavy at the base. Left unpruned, four- or five-year-old plants will grow to a normal average of 6 or 8 feet in height; under the most favorable conditions they will reach 10 feet; under the most adverse conditions it will amount to a vigorous shrub.

Blooming habit: Very profuse bloomer, producing more flowers than any other climbing rose variety known to me. It blooms continuously throughout the season. Compared with its parent, New Dawn, which itself has heretofore been considered one of the best everblooming climbers, my new variety will bloom four or five times as heavily during the same periods of the year.

Disease resistance: In common with other climbers, this variety is quite resistant to blackspot.

Cold resistance: This variety has stood up well under average winters of northern Ohio, but has not been tested in colder climates.

Stems:

*Type.*—Zigzagged. Internodes short.

*Strength.*—Very heavy.

*Color.*—Approximately Biscay Green (Pl. XVII), red-tinged, approximately Prussian Red (Pl. XXVII) on upper portion and sometimes for a distance of as much as 24 inches down from new growth.

*Thorns.*—Many very large thorns are found on the entire length of the stem. These are outward-pointing, red-tinged, very sharp, some almost a half inch long. They are irregularly placed although frequently appear in groups of three.

Foliage:

*Type.*—Odd pinnately compound, usually with 5 or 7 leaflets.

*Size.*—Medium; terminal leaflet being very much larger than any of the lateral leaflets. Terminal leaflet averages about 2 to 2¼ inches long and 1 to 1¼ inches wide.

*Quantity.*—Abundant.

*Texture.*—Substantial.

*Appearance.*—Central vein prominent.

*Shape.*—Long oval, pointed at base and tip. Approximately twice as long as wide.

*Edge.*—Sharply and finely serrated.

*Color.*—New foliage is predominantly red, approximately Van Dyke Red (Pl. XIII); turns green when it ceases to be succulent. Matured foliage is dark green, approximately Dark Dull Yellow Green (Pl. XXXII) on upper surface and frequently tinted with red, approximately Bordeaux Red (Pl. XII). Under surface is approximately Cress Green (Pl. XXXI).

*Rachis.*—Grooved and usually red-tinged above. Under surface same color as leaf, with occasional small prickles. Short from lower leaflets to stem, making leaves almost sessile.

*The bloom*

Bud:

*Form.*—Cone-shaped; wide at base and pointed. Before color shows, hooded sepals produce a long-pointed effect.

*Size.*—Medium.

*Color.*—Tight bud just beginning to show color is approximately Spinel Red (Pl. XXVI). Bud just beginning to unfurl is between Spinel Red (Pl. XXVI) and Rose Color (Pl. XII) on the outer surface with portion of inner petals showing lighter pink, approximately Eosine Pink (Pl. I). The color is uniformly spread, with no aiglet apparent.

*Sepals.*—Branched. Outside is same color green as stems. Reflex when bud begins to open.

*Peduncle.*—Very short, permitting foliage to come near flower to supply a good background; reddish-tinged; slender but strong.

The flower:

*Size.*—Medium. Averages about 4 inches in diameter when fully opened.

*Borne.*—Usually in clusters of from 3 to 8.

*Form.*—Full, high-centered form which is retained until the very last stages of opening when the center opens up to disclose the stamens and pistils.

*Petalage.*—Average is about 35 to 40 petals, with an additional 5 to 10 small petaloids.

*Color.*—The rose is completely bi-color, the outer surface of the petals of a full-blown rose being approximately Spinel Pink (Pl. XXVI), and the face of the petal Cameo Pink (Pl. XXVI), shaded slightly with Thulite Pink (Pl. XXVI). The partially opened flower is slightly darker on the outer surface, being at that stage between Rose Red and Rose Color (both Pl. XII), blending into Rose Pink (Pl. XII).

Petals:

*Shape.*—Almost round when lying flat, but reflex early into shield shape.

*Size.*—Average 1½ to 2 inches in diameter, for the outer petals.

*Texture.*—Not heavy but of fairly good substance.

*Appearance.*—Soft and silky.

*Persistence.*—Drop off cleanly when old.

*Fragrance.*—Pronounced and very pleasing.

*Lasting quality.*—Especially long-lasting as a cut flower.

Reproductive organs:

*Pistils.*—Many; grouped in center of flower; arise above stamens. Styles very slender and long; light yellowish-white, sometimes slightly red-tinged; topped by stigmas of light greenish-yellow.

*Stamens.*—Very large number; surround pistils. Filaments greenish-white; uneven lengths, some bent and twisted. Anthers medium size; mostly yellow, varying from Primuline Yellow (Pl. XVI) to Raw Sienna (Pl. III).

Having thus disclosed my invention, I claim:

The new and distinct variety of climbing rose plant, substantially as herein shown and described, characterized particularly by its new combination of vigorous growth with red new foliage; profuse and continuous everblooming habit; and perfection of bloom having excellent high-centered form, distinct fragrance, long-lasting qualities, and distinct bi-coloring in tones of pink.

CONRAD C. O'NEAL.

No references cited.